United States Patent [19]
Liu et al.

[11] Patent Number: 6,046,801
[45] Date of Patent: *Apr. 4, 2000

[54] LASER-BASED INSPECTION SYSTEM FOR OPTICAL DISKS

[75] Inventors: Gang Liu, Novi; Mark H. Schwartz, Orchard Lake, both of Mich.

[73] Assignee: Analog Technologies, Inc., Farmington Hills, Mich.

[ * ] Notice: This patent issued on a continued prosecution application filed under 37 CFR 1.53(d), and is subject to the twenty year patent term provisions of 35 U.S.C. 154(a)(2).

[21] Appl. No.: 08/997,440

[22] Filed: Dec. 23, 1997

[51] Int. Cl.$^7$ .................................................... G01N 21/16
[52] U.S. Cl. ..................... 356/237.1; 356/371; 356/376
[58] Field of Search ..................... 356/237, 239, 356/371, 376, 237.1–237.6; 359/197–205, 212–221

[56] References Cited

U.S. PATENT DOCUMENTS

| | | | |
|---|---|---|---|
| 3,667,846 | 6/1972 | Nater et al. | 356/376 |
| 3,790,287 | 2/1974 | Cuthbert et al. | 356/237.1 |
| 3,892,494 | 7/1975 | Baker et al. | 356/239.2 |
| 4,030,835 | 6/1977 | Firester et al. | 356/237 |
| 4,425,041 | 1/1984 | Nishiyama | 356/371 |
| 4,553,844 | 11/1985 | Nakagawa et al. | 356/376 |
| 4,832,487 | 5/1989 | Mikuriya et al. | 356/237 |
| 4,878,754 | 11/1989 | Homma et al. | 356/371 |
| 4,991,964 | 2/1991 | Forgey et al. | 356/371 |
| 5,025,268 | 6/1991 | Arimoto et al. | 359/205 |

Primary Examiner—Robert H. Kim
Attorney, Agent, or Firm—Harness, Dickey & Pierce, PLC

[57] ABSTRACT

A laser-based optical inspection system is provided for detecting and measuring surface imperfections and warpage conditions in an optical information storage disk either during its manufacture or afterwards. The optical inspection system includes a light source, a rotatable mirror for directing a source beam from the light source along a radial line on the surface of the disk, a convex lens positioned between the mirror and the disk for focusing the source beam at the surface of said disk, and a photodetector for registering a beam being reflected from the surface of said disk, such that the reflected beam is indicative of surface imperfections in said disk. In addition, an electronic processor and controller are connected to the photodetector for processing its registered beam signals and for determining if the disk surface imperfections exceeds specified tolerances. Furthermore, the processor may be used to control other system components, including the light source, the actuator device for rotating the mirror, and the drive motor for rotating the disk during the inspection process. These results about the warpage and any surface imperfection of the disk can be displayed on the monitor of the computer to inform the machine operator as well as sent to other related manufacturing machines for further usage.

19 Claims, 9 Drawing Sheets

LASER-BASED INSPECTION SYSTEM FOR OPTICAL DISKS

BACKGROUND OF THE INVENTION

1. Technical Field

This invention relates to a laser-based optical inspection system for inspecting products for flaws, and more particularly to a laser-based optical inspection system that detects and measures surface imperfections, including warpage, in optical information storage disks.

2. Discussion of Related Art

With all optical disks used for information storage, including analog and digital audio disks, compact digital disks (i.e., CDs) and digital video disks (DVD), it is important that these disks have a high degree of flatness. Because these types of disks are normally made of plastic, they can warp if subjected to sufficiently high temperatures or other thermal or mechanical stresses during the manufacturing process or afterwards. An audio record that has been too severely warped cannot be played. The same is true for optical disks. As technology has evolved, the storage capacity of optical disks has increased so that even slight warpage can impact the performance of the disks. A typical compact disk has a digital storage capacity of approximately 600 to 700 megabytes of information. Similarly, a new DVD has an even greater storage capacity (in the range of 4 to 16 gigabytes). As a result, optical components, such as the laser diodes and focusing systems used to read these disks, are much more precise and less tolerant of surface imperfections on the disks and of warped disk surfaces.

Due to the lack of equipment for quickly measuring warpage of optical disks, or quickly and inexpensively finding blemishes that would result in recording and playback errors, manufacturers often record information onto a disk, only to find out later that the disk was warped or has a surface blemish. Presently, a common quality control inspection approach for detecting the warpage of these disks is to play back the disk at a relatively high rate of speed. However, due to the immense storage volume of CD's and DVD's, the play back time (even on a sampling basis) for such disks is considerable, and cannot keep pace with the rest of the manufacturing processes.

Alternatively, visual detection methods using conventional camera systems are also utilized during quality control inspections by disk manufacturers. This method is limited to detecting imperfections on the surface of the disk, and although the detection resolution of this method is sufficient for inspecting audio disks, it is inadequate and/or too time-consuming for optical disks, particularly DVDs.

Currently, manufacturers of information storage disks require a low-cost, high-speed approach which can make high resolution measurements to test if a disk is flat within a desired degree of tolerance, and as to whether or not it has any unacceptable blemishes. In other words, manufacturers would like to be able to quickly and automatically inspect disks that are being fabricated in an automated line and reject those which have an excessive degree of tilt or warpage or which have unacceptable surface defects. At present, as far as we know, the industry is unaware of any simple, fast and practical means to detect warpage in an automated and speedy fashion.

Therefore, it is desirable to provide a high resolution and high speed optical inspection system for detecting and measuring warpage and other surface imperfections in optical information storage disks, especially DVDs. Since existing information storage disks are manufactured in a multiple step process, wherein laminated stacks of material are built up to produce a final disk product, it is also desirable to provide optical inspection equipment which can, if desired, perform inspection after each layer of the disk has been constructed and thus the present invention must operate at very high speed. Further, it is an object of the present invention to provide equipment used to detect disk warpage that is relatively compact and low cost, so that it does not add considerably to the space required for or the price of existing automated disk manufacturing facilities.

SUMMARY OF THE INVENTION

In light of the foregoing objects and to help solve the above-identified problems, there is provided, according to a first aspect of the present invention, an optical inspection system for detecting and measuring warpage or any other non-flat conditions in an optical information storage disk either during its manufacture or afterwards. The optical inspection system includes a light source, a rotatable reflective member for directing a source beam from the light source along a radial line on the surface of the disk, an optical lens positioned between the mirror and the disk for focusing the source beam at the surface of said disk, and at least one photodetector for registering a beam being reflected from the surface of said disk, such that the reflected beam is indicative of the warpage and surface imperfections in said disk. In addition, an electronic processor and controller, such as a standard personal computer, are connected to the photodetector for processing its registered beam signals and for determining if the disk has excessive warpage and/or contains any surface imperfections. Furthermore, the computer may be used to control other system components, including the light source, the actuator device for rotating the mirror, and the drive motor for rotating the disk during the inspection process. These results about the warpage and any surface imperfection of the disk can be displayed on the monitor of the computer to inform the machine operator as well as sent to other related manufacturing machines for further usage.

There is provided, according to a second aspect of the present invention, a laser-based optical inspection system for detecting and measuring surface imperfections, including warpage, flaws and defects, in optical information storage disks. More particularly, the optical inspection system comprises a monochromatic light source, such as a laser diode, a rotatable mirror, a convex lens and a four quadrant photodetector.

According to a third aspect of the present invention, there is provided a method for detecting surface imperfections in an optical disk. First, a light source is projected towards a rotatable reflective member, and then the light source is directed towards the surface of the disk using the reflective member. At least one optical lens is positioned between the reflective member and the disk for passing the light source, as well as guiding the light being reflected from the disk towards a photodetector. Finally, the reflected light source is registered by the photodetector, such that the reflected light source is indicative of a surface condition of said disk.

These and other aspects, objects, features and advantages of the present invention will be more fully understood from the following detailed description, drawings and appended claims.

BRIEF DESCRIPTION OF THE DRAWINGS

Other objects and advantages of the present invention will be apparent to those skilled in the art upon reading the following detailed description and upon reference to the drawings in which.

DETAILED DESCRIPTION OF THE PREFERRED EMBODIMENTS

The following description of the preferred embodiments of the laser-based inspection systems of the present invention are merely exemplary in nature and are in no way intended to restrict the scope of the present invention or its application or its uses.

Figure 1:
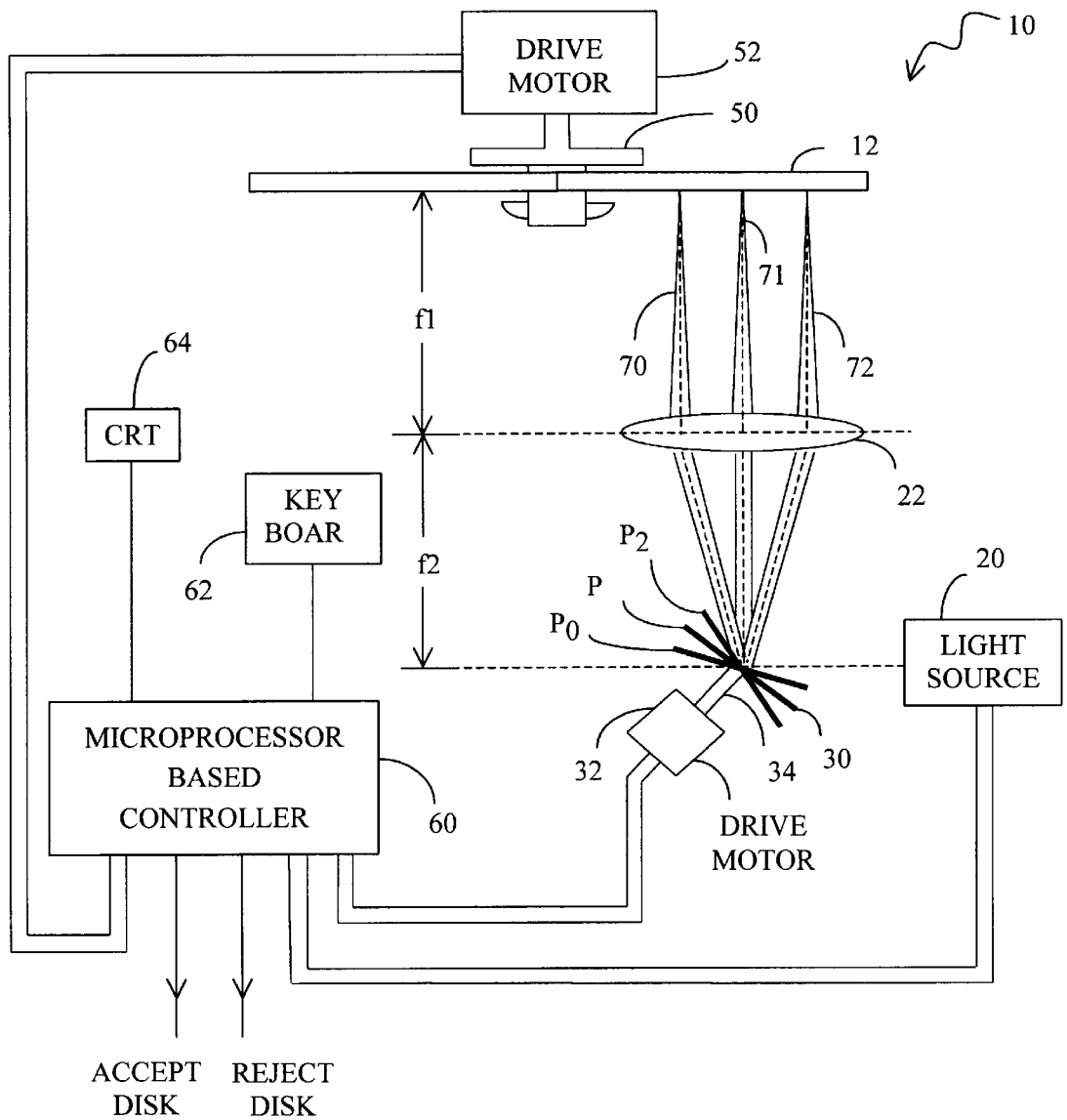
FIG. 1 is a side plan view in block diagram form showing the basic components of a first embodiment of a laser-based optical inspection system of the present invention.

A laser-based optical inspection system 10 for detecting surface imperfections in optical information storage disks 12 is illustrated in FIG. 1. The basic components of optical inspection system 10 include a monochromatic light source 20, a rotatable mirror 30 for directing the light source towards the disk surface through a convex lens 22, resulting in the scanning beams 70, 71 and 72 when the mirror rotates from positions $P_0$, $P_1$ to $P_2$, respectively, and a photodetector 40 (not shown) for registering the reflected light source 20. Due to its monochromatic properties, a laser beam light source, such as a diode laser, is preferred over other light sources because of its ability to keep its optical beam in focus.

Figure 2A:
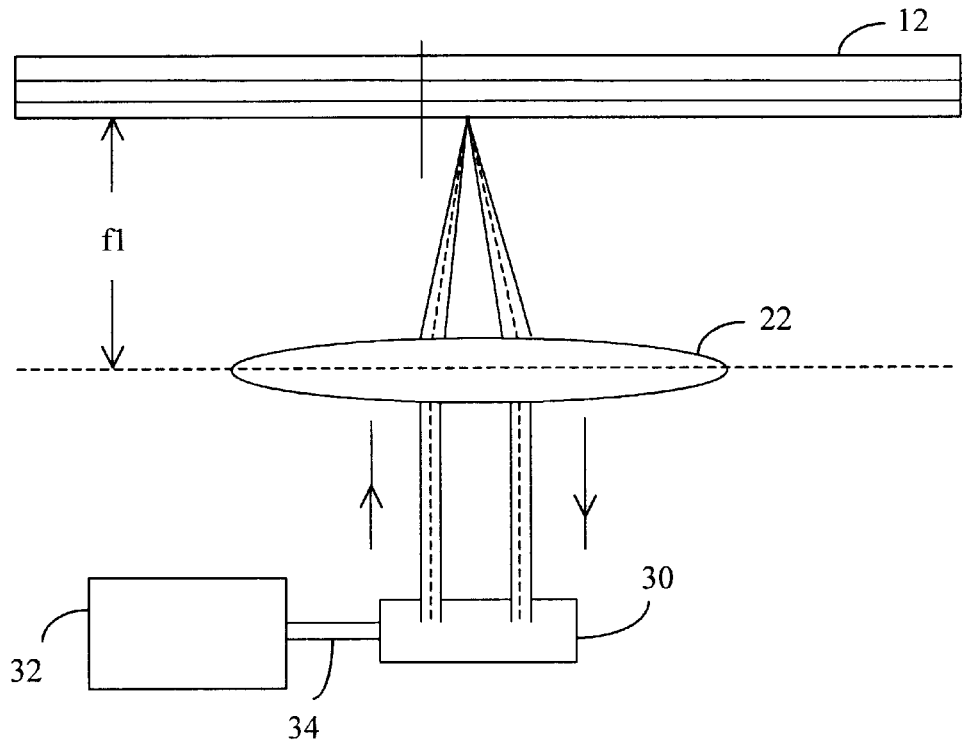
FIG. 2A is a front view showing a focal length at the surface of a disk in the first embodiment of the optical inspection system of the present invention.
Figure 2B:
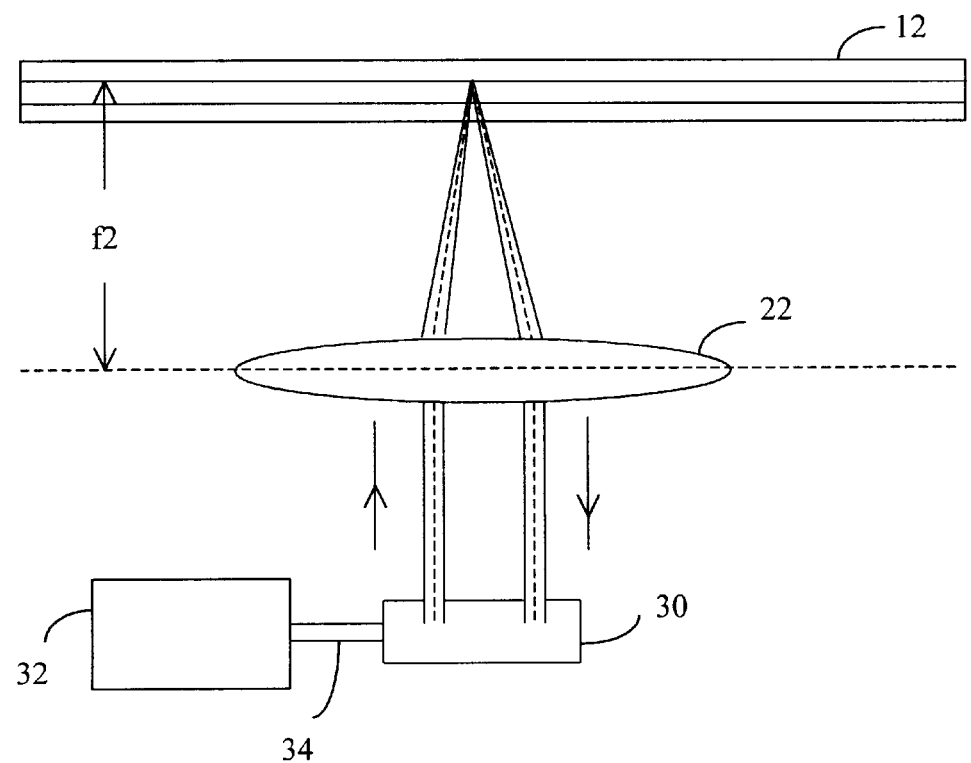
FIG. 2B is a front view showing a focal length at an interior layer of the disk in the first embodiment of the optical inspection system of the present invention.

Convex lens 22 is positioned between mirror 30 and disk 12 for focusing light source 20 towards the reflective surface of disk 12. The plane of lens 22 and the plane of disk 12 are aligned in parallel. Convex lens 22 may be provided with focal lengths $f_1$ and $f_2$ which are equal (as shown) or different. It is preferred to have the reflective surface of disk 12 be at focal length $f_1$ on the disk side of lens 22 and to have focal length $f_2$ be the distance between the center of lens 22 and the center point of reflection on mirror 30. Focal length $f_2$ serves to ensure that all of the scanning light beams 70, 71 and 72 remain parallel to each other, and thus are reflected back along the same exact path through lens 22. Focal length $f_1$ serves to ensure that all the scanning beams 70, 71 and 72 will be focused on the disk, and will have the beam spot size minimized. Thus, the greatest resolution in both surface defect (or flaw) detection and warpage (or tilt) measurement will be achieved. As best seen in FIG. 2B, it is also envisioned that an interior layer of disk 12 may be at focal length $f_1$. Therefore, optical inspection can occur not only on the surface of disk 12, but also at an interior layer.

In FIG. 1, the rays of light passing through lens 22 will be directed orthogonally to the reflective surface of disk 12 and then reflected back through the same path, as long as disk 12 is not warped. If the disk is warped, even slightly, the return path will be offset somewhat from the original beam path. Those skilled in the art will recognize that the light beams between mirror 30 and lens 22 are arranged so as to focus reflected light beams on the center of mirror 30. It is also envisioned that single convex lens 22 may be replaced with a multiple segment lens, a series of lenses, or a lens of another kind, if desired.

Figure 3:
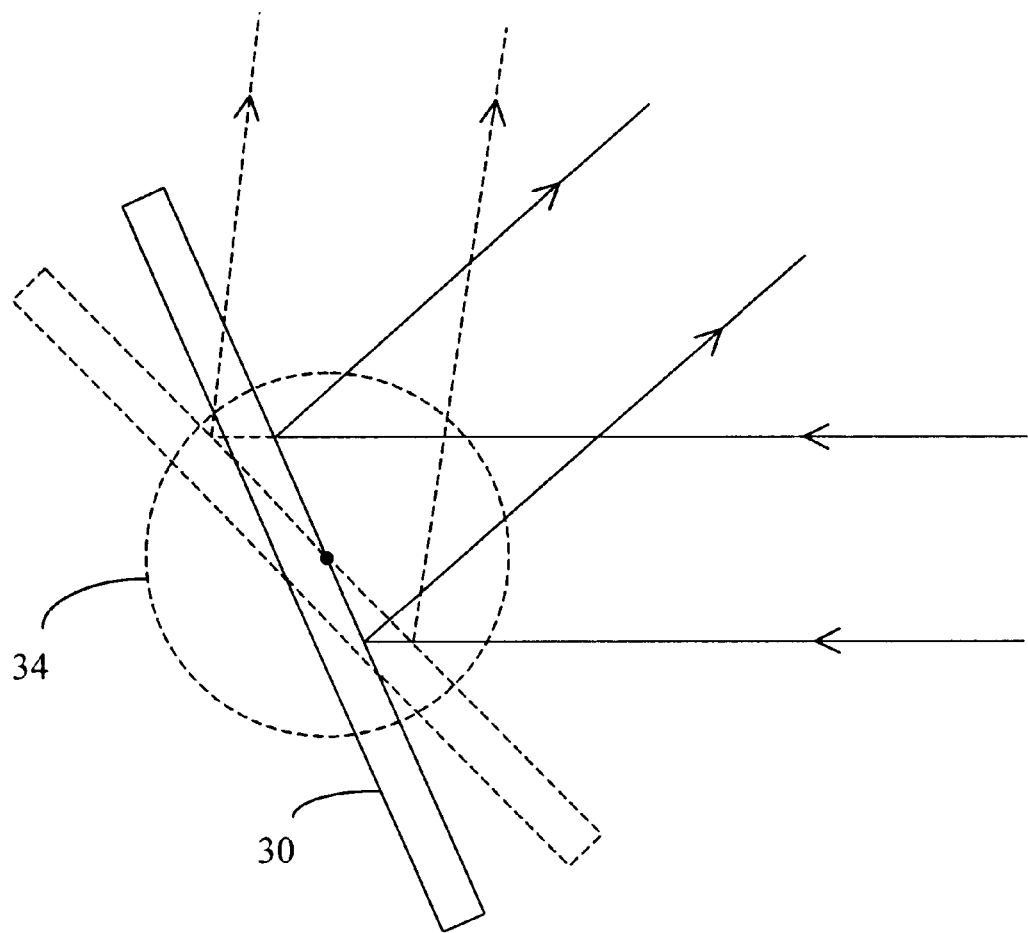
FIG. 3 is a fragmentary side view showing the movement mechanism of a mirror in the first embodiment of the present invention, which may be arranged to swivel or to rotate.

Rotating or oscillating mirror 30 is comprised of a regular flat mirror. Referring to FIGS. 1–3, the rotating mirror 30 can be moved about a vertical rotating shaft 34 so as to sweep the source beam through lens 22 and across the surface of disk 12. The rotating or swivelling motion of mirror 30 may be achieved by use of an analog or digitally controlled motor 32 or any other suitable proportional actuation device connected to rotating shaft 34. Those skilled in the art will also appreciate that mirror 30 may be rotated in a 360° continuous pattern, with the option of having the laser beam from light source 20 being turned on and off at the appropriate time so as to achieve the desired tracking across the surface of disk 12. Alternatively, photodetector 40 or other suitable sensing equipment may be turned on and off, and light source 20 kept on continuously to achieve this same result. It is also envisioned that a non-flat mirror design could be implemented in the present invention, so long as (by using known principles of optics) the reflected beam is directed back to detector 40.

In a first embodiment of the present invention, the laser light source 20 also functions as a detection device. Since a detectable effect is produced when the reflected beam is directed directly back into the source beam, light source 20 can be used to detect when the beam of light is out of focus. As the beam of light is swept across a flat disk, the strength of the reflected beam as detected by light source 20 should remain substantially constant. Any deviation from this constant value can be detected. Once above a predetermined limit, this deviation serves as an indication that disk 12 is warped beyond an acceptable tolerance. However, at the present time, although representing a possible alternative embodiment of the present invention, this configuration is not the preferred approach.

Figure 4:
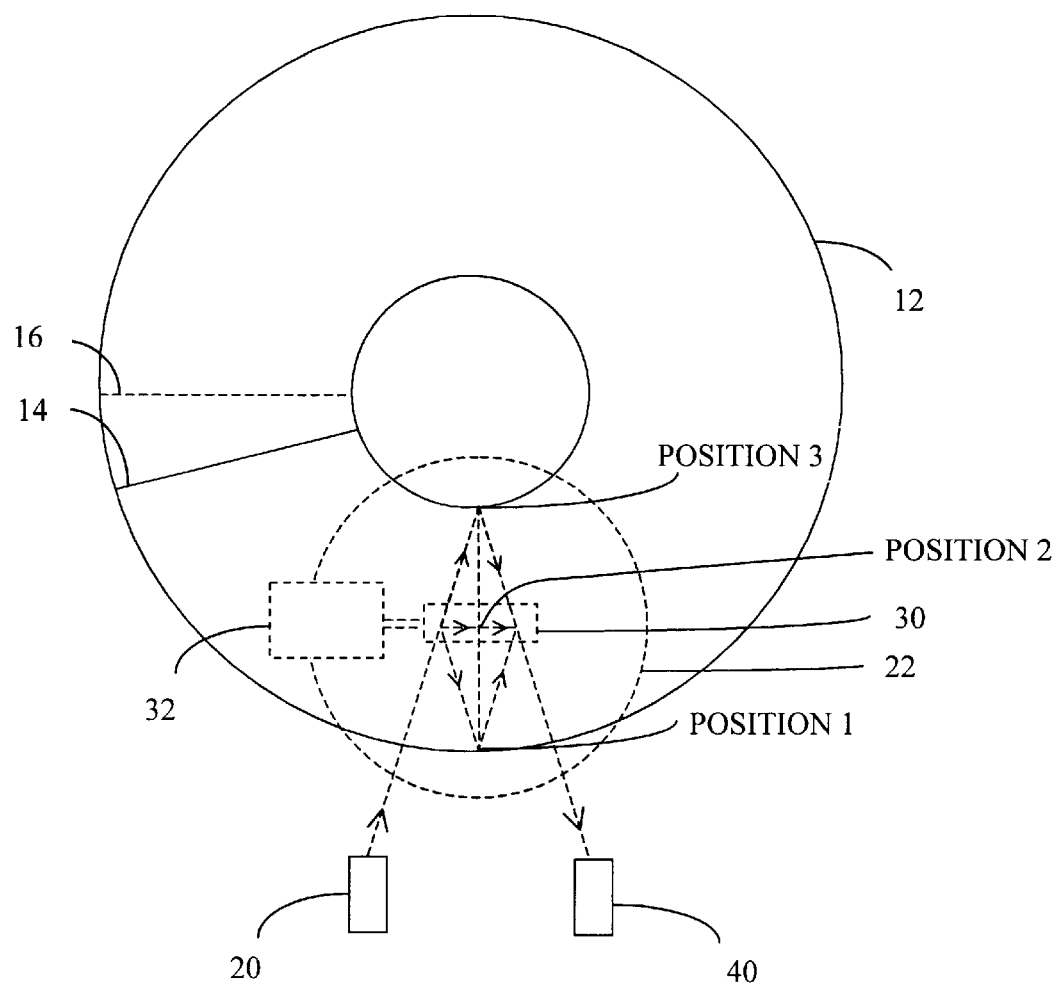
FIG. 4 is a top view showing an offset photodetector in a second preferred embodiment of the optical inspection system of the present invention.

In a second preferred embodiment, the source beam is reflected off mirror 30, through lens 22, reflects off disk 12, returns through lens 22, and then is registered by a photodetector 40 which is offset from light source 20 as shown in FIG. 4. This slight angular displacement may be achieved by positioning the angle of light source 20 off the orthogonal angle of mirror 30 so as to allow the reflected beam from a flat disk 12 to be registered in the exact center of photodetector 40. As shown in FIG. 2 and FIG. 4, by rotating mirror 30 the source beam of light is directed to three different locations along the surface of disk 12, and yet each reflected beam of light strikes photodetector 40.

Therefore, to inspect disk 12, mirror 30 and lens 22 are configured to scan (or sweep) a single radial line 14 across disk 12. Those skilled in the art will appreciate that a continuous track across radial line 14 of disk 12 may not be required. Rather, it is possible to have a sampled line 16, as represented by the dotted line. However, to achieve 100% surface inspection along a radial line, it is preferred to have sampling dots as close together as possible (if not entirely continuous).

Figure 5:
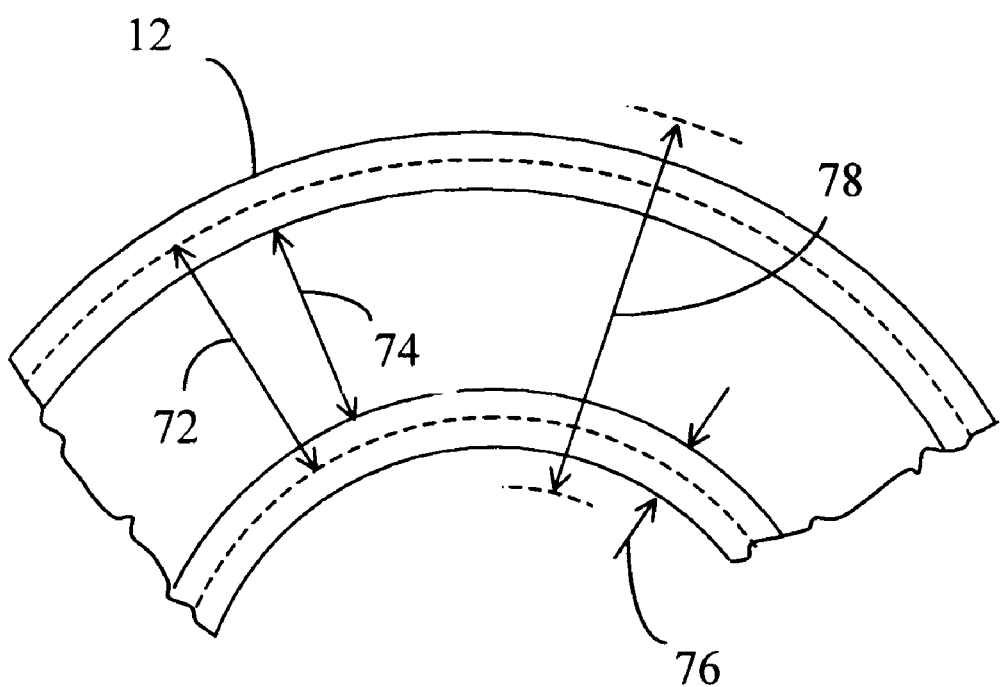
FIG. 5 is a fragmentary top view showing an optical disk used in the optical inspection system of the present invention.

With regards to defining a scanned region, a typical optical disk 12 is illustrated in FIG. 5. Disk 12 comprises an information storage region 74 defined within a metallization region 72 that has been deposited onto the plastic base of disk 12. A human readable/bar code region 76 is also defined along the inner edge of disk 12. A scanned region 78 to be inspected by optical inspection system 10 is defined outside the physical boundaries of disk 12. As will be apparent to one skilled in the art, optical inspection system 10 should be configured to handle surface imperfections detected outside information storage region 74 (but within scanned region 78) by either turning light source 20 on and off at appropriate times or by ignoring data collected from outside storage region 74.

To inspect the entire disk surface, disk 12 will be rotated during the inspection process. As shown in FIG. 1, a spindle 50 includes a conventional collapsible mandrel or chuck 51 that releasably attaches to disk 12 by passing through the center circular opening of disk 12. A drive motor 52 connects to spindle 50 to rotate disk 12 by rotating the mandrel 51 concentrically mounted on the spindle 50, after the mandrel 51 has been expanded to firmly engage the inner rim of disk 12. An alternative embodiment for rotating the disk is to place the disk drive motor under the disk. This embodiment is more preferable because it is easier to load and unload the disk. If disk 12 is rotated one degree per sweep, 360 radial lines of resolution will be used to inspect the entire disk surface. At present, to ensure that any warpage in disk 12 will be detected, it is preferred to utilize a scanning resolution in the range of 90 to 720 radial lines per disk, with 250 to 400 lines being the preferred resolution. For a more thorough surface inspection of disk 12, it would be desirous to use several thousand contiguous and even overlapping radial lines during the inspecting process. Alternatively, rotatable mirror 30 and lens 22 may be configured so that the beam is swept across the entire diameter of disk 12, and not merely across a radial length. Although scanning patterns which are radial in nature have been discussed above, it is also envisioned that non-radial scanning patterns can also be implemented for inspecting disks in the present invention, such as a raster-like scan pattern used on CRTs, an X-Y grid of horizontal and vertical lines, or circular patterns around the center of the disk.

To control optical inspection system 10, a controller 60 has been incorporated. Controller 60 may be implemented by using a standard PC computer, including a microprocessor, random access memory (RAM), read-only memory (ROM), and electrically erasable, programmable read-only memory (EEPROM), connected to a keyboard 62 and CRT 64. In addition, controller 60 has provisions for digital and analog input and output (I/O) circuits or ports for powering and controlling various system components. Light source 20, mirror drive motor 32, and disk rotation drive motor 52 can each be connected to and controlled by controller 60, or run independently. One skilled in the art will readily recognize that by using conventional techniques, control software and different controller configurations are easily realized for optical inspection system 10. Moreover, controller 60 connects to photodetector 40 for processing the registered location of the reflected beam and for determining if a measured disk falls within acceptable tolerances.

Figure 6:
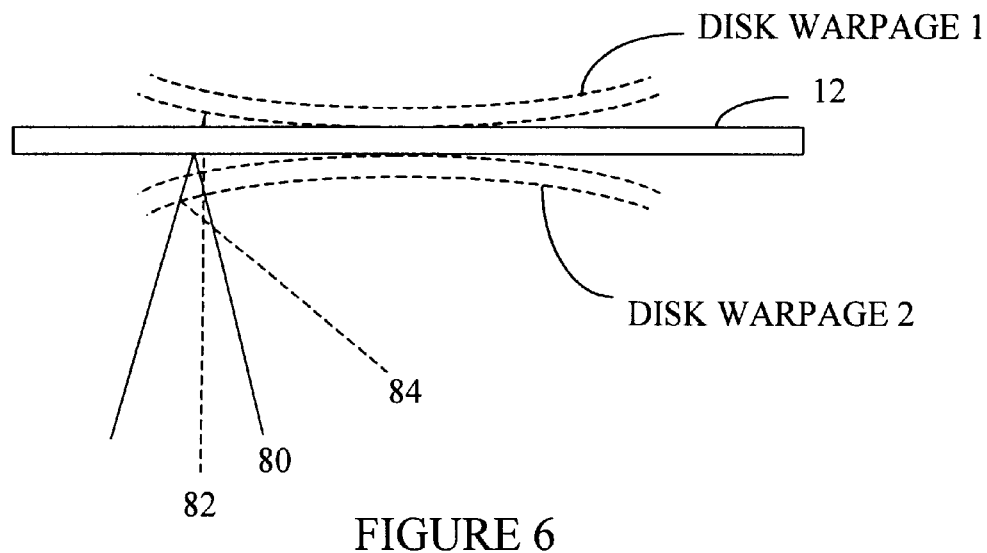
FIG. 6 is a fragmentary side view showing three source beams and their corresponding reflected beams from an optical disk with varying degrees of flatness to further illustrate some of the optical principles of operation of the present invention.
Figure 7A:
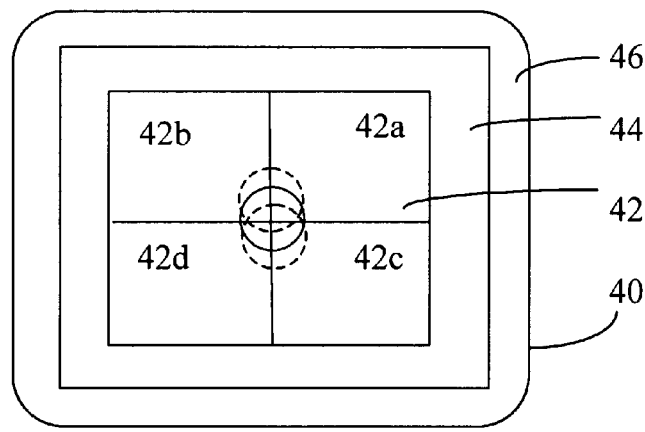
FIG. 7A is an enlarged side elevational view of a four quadrant photodetector used in the optical inspection system of the present invention.
Figure 7B:
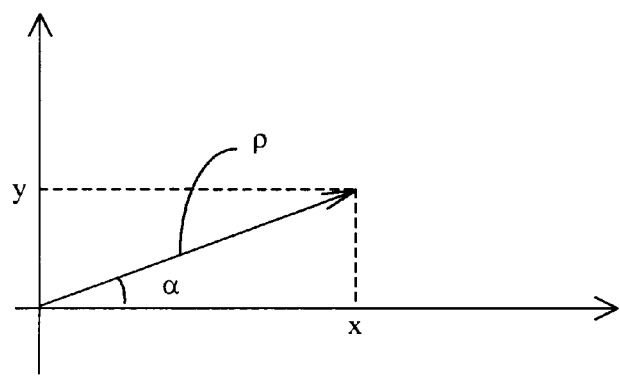
FIG. 7B is a diagram showing a Cartesian coordinate system and a Polar coordinate system for determining reflected beam displacement in photodetector.

In operation, the first reflected beam 80 for a flat disk will be registered at the center of photodetector 40. Depending upon the nature of the warpage, disk 12 will offset a second reflected beam 82 (disk warpage 1) or a third reflected beam 84 (disk warpage 2) as seen in FIG. 6, depending upon which direction the disk is warped. FIG. 7 shows a close-up view of a four quadrant photodetector 40, further comprised by an active electro-optic receiver 42 having four distinct electrically isolated receiving elements 42a, 42b, 42c and 42d, a substrate support structure 44 for holding the elements 42a–42d thereon, and a photodetector housing 46. One detector element (42a, 42b, 42c and 42d) is in each quadrant as shown. First, the reflected beam 80 registers at the center of photodetector 40 indicating a flat disk surface. However, a warped disk will cause second reflected beam 82 or a third reflected beam 84 to be returned to off-center positions in photodetector 40. The imbalance of more light striking one quadrant and less light striking the other quadrants is detected by inspection system 10. When the amount of imbalance in terms of reflected light is sufficiently high, it will exceed a predetermined limit and thus provide an indication that disk 12 is warped. In addition, the use of a quadrant decoder allows the optical inspection system 10 to determine the degree of warpage (or angle of tilt) in disk 12 by applying the following equations:

$$x = \frac{a-b+c-d}{a+b+c+d} \quad y = \frac{a-c+b-d}{a+b+c+d}$$

$$\text{Magnitude } \rho = \sqrt{x^2 + y^2} \quad \text{Angle } \alpha = \tan^{-1}\frac{x}{y},$$

where
a=the amount of light received by detector 42a;
b=the amount of light received by detector 42b;
c=the amount of light received by detector 42c;
d=the amount of light received by detector 42d.
As shown in FIG. 7B, x and y are the relative displacements of a beam spot on the quadrant detector in the x and y directions, respectively; whereas ρ and α are the coordinates of the beam spot displacement in a polar coordinate system. The tilt or warpage angle of the disk in the location of the beam spot can be calculated as:

$$\Theta = \frac{1}{2} \text{arc tan} \frac{\rho}{L},$$

where:
L is the length of the optical path the reflected beam travels from the disk to the quadrant photo detector, when this angle is small which holds true in most practical cases.
The total reflectance of the surface from the current spot undergoing detection can also be monitored using the sum of the values of reflected light represented by a, b, c, and d. By summing these values, particularly on a pixel by pixel basis, the surface quality, in terms of total reflectance, can be detected. Thus, surface defects and/or surface flaws can be found and measured. Measurement signals are sent from photodetector 40 to controller 60. Using these above-referenced equations, controller 60 will generate output signals indicative of the warpage and/or surface quality of disk 12. Controller 60 may then be interfaced into the disk manufacturing process to automatically accept, reject, and/or classify each inspected disk, as well as provide input for other quality control systems. It may be useful to have two or more levels of detection so that a first level can serve as a warning when disk warpage begins to exceed acceptable tolerances during the manufacturing process.

Figure 8:
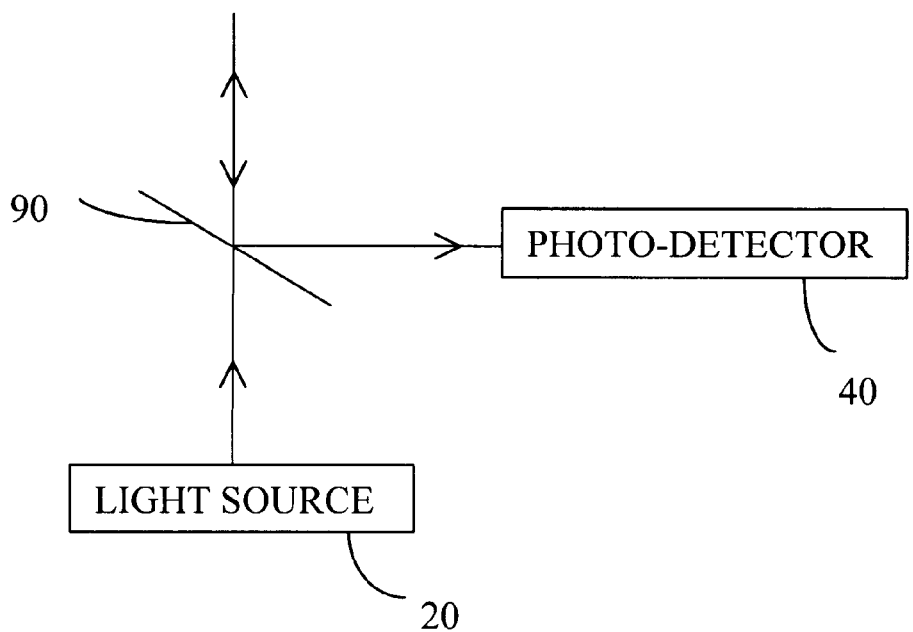
FIG. 8 is a fragmentary top view showing an alternate embodiment of the optical inspection system using a partially reflecting mirror arrangement to reflect the returning beam towards a photodetector in the present invention.
Figure 9:
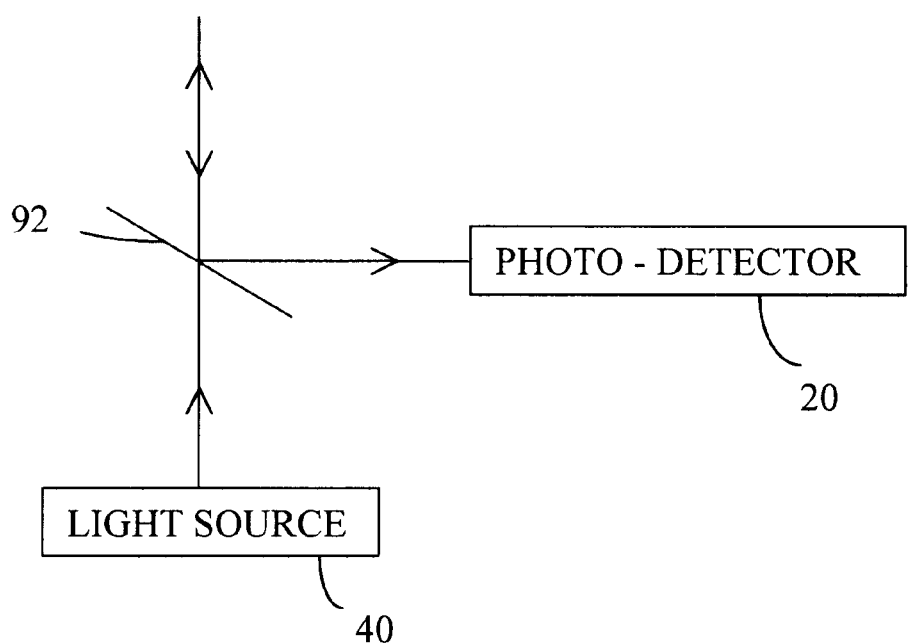
FIG. 9 is a fragmentary top view showing a second alternate embodiment of the optical inspection system using a partially reflective mirror to pass through the returning beam towards a photodetector in the present invention.

An alternative embodiment is shown in FIG. 8, where a partially reflecting mirror 90 is arranged on a 45° angle from the axis of light source 20. The reflected beam normally comes straight back along the same (or slightly different) path as the source beam, but the partially reflecting mirror 90 takes part of the reflected beam and directs it on an angle to photodetector 40. Similarly, a partially reflecting mirror 92 may reflect the source beam at a 45° angle into its measurement path, and then allow some part of the reflected beam to pass through the mirror to reach photodetector 40 as seen in FIG. 9. The return beam path may also be slightly different. Although the various configurations of the present invention have described system components as being at 45° angles with respect to each other, these components may be arranged at any suitable angle so long as the system adheres to the basic principles discussed above.

Figure 10A:
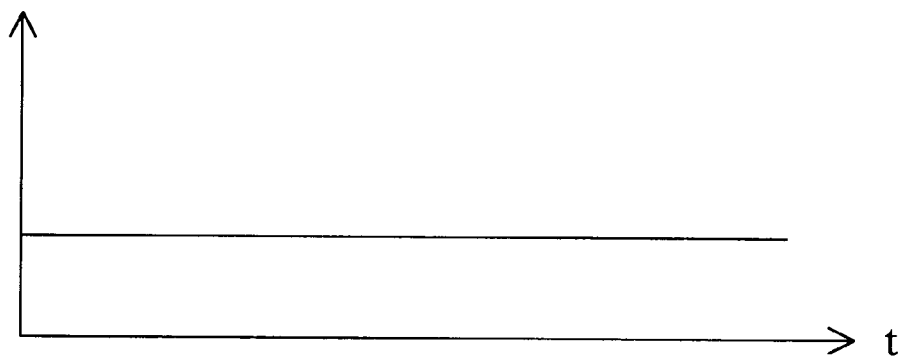
FIGS. 10A and 10B illustrate the laser beam power without modulation and with modulation, respectively, as may be employed in the present invention.
Figure 10B:
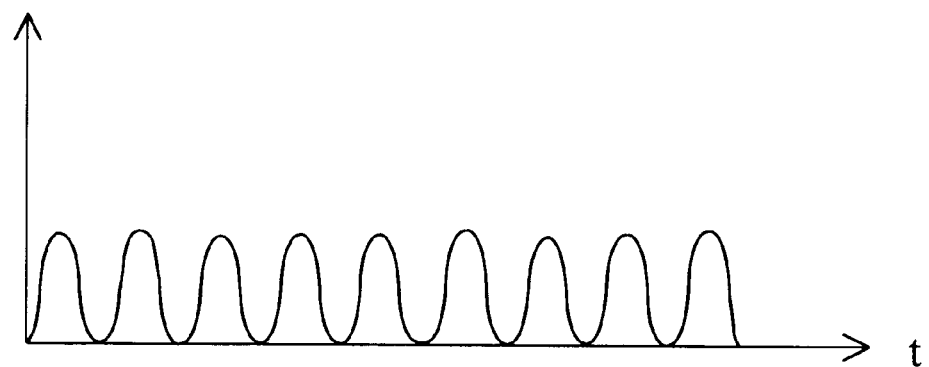
Figure 11A:
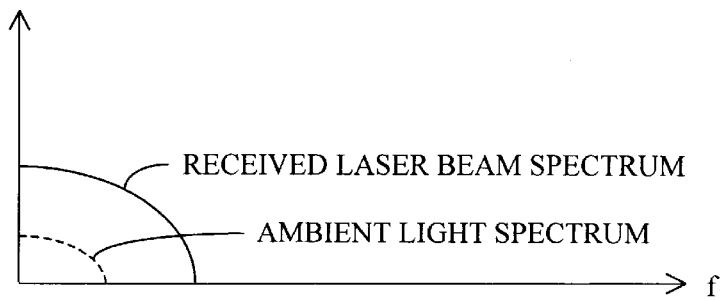
FIGS. 11A and 11B illustrate the receiving laser beam spectrum without modulation and with modulation, respectively, as may be employed in the present invention.
Figure 11B:
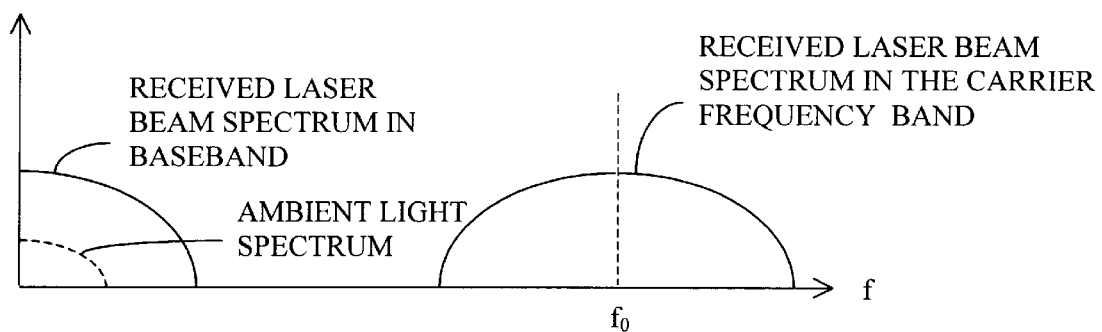

Referring to FIGS. 10 and 11, surface irregularities, such as problems with the metallized film region, can be detected using this optical inspection system 10. A laser beam can operate at a high frequency, and therefore can be modulated at high speeds (above 1 MegaHertz). With a suitable photodetector, a point by point inspection of the surface reflection coefficient for disk 12 can be made using inspection system 10. Although it is possible to modulate a laser beam at 100 MegaHertz, the basic intention is to modulate the laser beam at a frequency substantially above the frequency spectrum of incident light found in the manufacturing environment (i.e., 60 Hertz and its harmonics from fluorescent lights). Thus, if the laser beam were modulated at a frequency in the range of 1 MegaHertz (up to 10 MegaHertz or more), a frequency filter centered about the specified frequency of laser beam modulation could be used as a technique for screening out any and all natural light interferences which may have been received by the photodetector.

One benefit of using a modulated laser light beam is that it is possible to have the total average power output of the laser beam be reduced to acceptable safety limits so as to not pose a threat for eye injuries within the industrial environment. Another advantage is that a modulated laser beam can be operated "more coolly" than a continuously pumped laser beam. For achieving the same peak power, those skilled in the art will appreciate that modulated laser beam devices are frequently operated at cooler temperatures and/or without a heat sink; whereas a continuous laser beam may require a heat sink. In addition, the useful expected life of a laser diode is directly related to its total continuous power output, and thus the equipment can be operated for longer periods of time if the light is pulsed at the same peak power but with a much lower average power. Finally, by having the laser beam pulse modulated, the peak beam power of the laser can be raised, while having the average beam power remain the same or lowered. The peak signal to noise ratio at the photodetector will be increased, thereby resulting in improved reliability and capability of surface flaw detection and improved warpage (tilt) measurements of the disk.

The foregoing discloses and describes merely exemplary embodiments of laser-based optical inspection systems and methods of the present invention. One skilled in the art will readily recognize from such discussion, and from the accompanying drawings and claims, that various changes, modifications and variations may be made therein without departing from the spirit and scope of the present invention. For instance, although this invention has been discussed with respect to a disk that rotates so that a stationary beam is swept in only one plane, those skilled in the art will recognize that a stationary disk may also be utilized. With a stationary disk, the source beam is caused to rotate by a mirror that not only oscillates in one direction, but in fact oscillates in two directions. In this manner, it is not necessary to rotate the disk. Instead, the mirror can have two degrees of freedom and a source beam can be swept in various patterns (if necessary, turned on and off at appropriate times) to achieve the inspection of any desired disk. Additionally, the optical inspection system of the present invention may be used not only in the manufacturing process, but may also be used in consumer optical equipment to determine whether or not a disk contains surface imperfections that may impair the disk performance.

Those skilled in the art will appreciate from the foregoing description that the broad teachings of the present invention can be implemented in a variety of forms. Therefore, while this invention has been described in connection with particular examples thereof, the true scope of the invention should not be so limited since other modifications will become apparent to the skilled practitioners upon a study of the drawings, specifications and following claims.

We claim:

1. An optical inspection system for detecting surface imperfections in an optical disk, comprising:

a light source;

a rotatable reflective member having a substantially planar reflective surface for directing a source beam from said light source towards said disk and for guiding a reflected beam being reflected from said disk;

an actuator device coupled to said reflective member for rotating said reflective member about an axis of rotation, the planar reflective surface of said reflective member being precisely aligned with the axis of rotation of said actuator device;

at least one optical lens positioned between said reflective member and said disks for directing focusing said source beam at the surface of said disk and for guiding said reflected beam back to said reflective member; and a photodetector for registering said reflective beam, wherein said reflected beam is indicative of a surface condition of said disk.

2. The optical inspection system of claim 1 wherein said surface condition includes at least one of a surface defect, a surface flaw, and a warped surface.

3. The optical inspection system of claim 1 further comprising a controller connected to said photodetector for processing said registered beam and for determining said surface condition of said disk.

4. The optical inspection system of claim 1 wherein said source beam is focused at an interior layer of said disk and a reflected beam being reflected from the interior layer of said disk, wherein said reflected beam is indicative of a surface condition of the interior layer of said disk.

5. The optical inspection system of claim 1 wherein said optical lens directs said source beam orthogonally towards said surface of said disk.

6. The optical inspection system of claim 1 further comprising a rotatable spindle for releasably attaching to said disk and a drive motor coupled to said spindle for rotating said disk, thereby inspecting a plurality of radial lines on the surface of said disk.

7. The optical inspection system of claim 6 wherein said controller connected to said light source, said actuator device and said drive motor for controlling said light source, said actuator device and said drive motor.

8. The optical inspection system of claim 1 wherein said rotatable reflective member further comprises a partially reflective mirror, whereby said reflected beam is directed by said reflective mirror towards said photodetector positioned at a 45° angle with respect to axis of said source beam.

9. The optical inspection system of claim 1 wherein said rotatable reflective member further comprises a partially reflective mirror, whereby said reflected beam passes through said reflective mirror to said photodetector, wherein said light source is directed towards said reflective mirror at a 45° angle with respect to axis of said reflected beam.

10. The optical inspection system of claim 1 wherein the distance between a principal point of said optical lens on the reflective member side thereof and the center incident point of said source beam on said reflective member is equivalent to the focal length of said reflective member side.

11. The optical inspection system of claim 1 wherein the distance between a principal point said optical lens on said disk side thereof and the center incident point of said source beam on said disk is equivalent to the focal length of said optical lens on said disk side.

12. An optical inspection system for detecting surface imperfections in optical disks, comprising:

a monochromatic light source;

a rotatable mirror having a substantially planar reflective surface for directing a source beam from said light source toward said disk and for guiding a reflected beam being reflected from said disk;

an actuator device coupled to said rotatable mirror and being operative to rotate said rotatable mirror about an axis of rotation, the planar reflective surface of said mirror being precisely aligned with the axis of rotation of said actuator device;

a convex lens positioned between said mirror and said disk for focusing said source beam at the surface of said disk and for guiding said reflected beam back to said rotatable mirror; and a four quadrant photodetector for registering said reflected beam, wherein the location of said reflected beam striking said photodetector is indicative of a surface condition of said disk.

13. The optical inspection system of claim 12 wherein said surface condition incudes at least one of a surface defect, a surface flaw, and a warped surface.

14. The optical inspection system of claim 12 further comprising a computer connected to said photodetector for processing said registered beam and for determining if said disk contains any surface imperfections.

15. The optical inspection system of claim 12 wherein said light source comprises a modulated monochromatic light source for separating polychromatic light registered in said photodetector to increase the signal to noise ratio.

16. The optical inspection system of claim 12 further comprising a rotatable spindle for releasably attaching to said disk and a drive motor coupled to said spindle for rotating said disk, thereby inspecting a plurality of radial lines on the surface of said disk.

17. The optical inspection system of claim 16 wherein said controller connected to said light source, said actuator device and said drive motor for controlling said light source, said actuator device and said drive motor.

18. A method for detecting surface imperfections in an optical disk by radially sweeping the disk with a beam of focused light, comprising the steps of:

projecting a light source toward a rotatable reflective member having a substantially planar reflective surface;

directing said light source toward the surface of said disk using said reflective member by rotating said reflective member about an axis of rotation precisely aligned with the planar reflective surface; and focusing said light source at the surface of said disk using at least one optical lens positioned between said reflective member and said disk;

passing said light source being reflected from said disk through said optical lens;

guiding said light source being reflected from said disk to a photodetector using said reflective member; and registering said reflected light source, wherein said reflected light source is indicative of a surface condition of said disk.

19. The method of claim 18 further comprising the step of rotating said disk with respect to said light source, thereby inspecting a plurality of radial lines on the surface of said disk.

* * * * *

UNITED STATES PATENT AND TRADEMARK OFFICE
CERTIFICATE OF CORRECTION

PATENT NO.    : 6,046,801
DATED         : April 4, 2000
INVENTOR(S)   : Gang Liu and Mark H. Schwartz Page 1 of 1

It is certified that error appears in the above-identified patent and that said Letters Patent is hereby corrected as shown below:

<u>Column 8,</u>
Line 50, Claim 1, after "focusing" insert -- of --.
Line 53, Calim 1, delete "reflective" and insert -- reflected --.

<u>Column 9,</u>
Line 10, Claim 7, before "connected" insert -- is --.
Line 30, Claim 11, after "point" insert -- of --.

Signed and Sealed this

Eleventh Day of September, 2001

*Attest:*

*Nicholas P. Godici*

*Attesting Officer*

NICHOLAS P. GODICI
*Acting Director of the United States Patent and Trademark Office*